United States Patent
Wilson, Jr.

(10) Patent No.: US 7,326,223 B2
(45) Date of Patent: *Feb. 5, 2008

(54) LIGATING CLIP WITH INTEGRAL CUTTING GUIDE

(75) Inventor: Donald F. Wilson, Jr., Raleigh, NC (US)

(73) Assignee: Teleflex Medical Incorporated, Limerick, PA (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/763,033

(22) Filed: Jan. 22, 2004

(65) Prior Publication Data

US 2005/0165422 A1 Jul. 28, 2005

(51) Int. Cl.
*A61B 17/45* (2006.01)
*A61B 17/08* (2006.01)
*A61B 17/32* (2006.01)
*A45D 20/08* (2006.01)
*A45D 8/00* (2006.01)
*A45D 8/22* (2006.01)

(52) U.S. Cl. .............. 606/157; 606/151; 606/120; 606/170; 132/271; 132/276; 132/278

(58) Field of Classification Search .......... 606/151, 606/170, 178, 179, 256, 250, 157, 120; 132/278, 132/277, 279

See application file for complete search history.

(56) References Cited

U.S. PATENT DOCUMENTS

| | | | |
|---|---|---|---|
| 4,834,096 A | 5/1989 | Oh et al. | |
| 5,062,846 A * | 11/1991 | Oh et al. | 606/158 |
| 5,100,416 A | 3/1992 | Oh et al. | |
| 5,713,911 A * | 2/1998 | Racenet et al. | 606/157 |
| 6,391,035 B1 | 5/2002 | Appleby et al. | |
| 6,863,675 B2 * | 3/2005 | Wilson, Jr. | 606/157 |
| 2003/0069589 A1 * | 4/2003 | Small | 606/120 |

* cited by examiner

Primary Examiner—(Jackie) Tan-Uyen Ho
Assistant Examiner—Melissa Ryckman
(74) Attorney, Agent, or Firm—Baker & Hostetler LLP (57) ABSTRACT

A polymeric, surgical clip having first and second curved legs with each having a pair of opposing side surfaces joined at their proximal ends by a flexible hinge section and movable from an open position to a closed position for clamping a vessel between curved opposing inner surfaces. The first leg terminates at its distal end in a female locking member, and the second leg member terminates in a male locking member complimentary to the female locking member such that when the first and second leg members are moved from an open position to a closed position about the hinge section the male member is lockingly engaged in the female locking member. The clip has at least one cutting guide extending outward from and disposed along at least a portion of the length of at least one of the side surfaces of at least one of the first and second legs. The cutting guide aids in cutting the ligated tissue a safe distance from the clip such that a tissue cuff is formed.

30 Claims, 7 Drawing Sheets

LIGATING CLIP WITH INTEGRAL CUTTING GUIDE

TECHNICAL FIELD

The present disclosure relates to surgical clips, and more particularly to ligating clips with integral cutting guides to facilitate properly cutting vessels and other tissue to be clamped by the surgical clip, such that a safe amount of tissue remains extending from the cutting side of the clip. Yet more particularly, the present disclosure relates to an improved surgical ligating clip that is provided with one or more cutting guides extending outward from and disposed along at least a length of one or more opposing side surfaces of the clip.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Typically, a clip is applied to the vessel or other tissue by using a dedicated mechanical instrument commonly referred to as a surgical clip applier, ligating clip applier, or hemostatic clip applier. Accordingly, the use of ligating clips in endoscopic as well as open surgical procedures has grown dramatically.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, well known polymeric clips are disclosed in U.S. Pat. No. 4,834,096 to Oh et al. and U.S. Pat. No. 5,062,846 to Oh et al., both of which are assigned to the assignee of the presently disclosed subject matter. These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place.

The distal ends of the clips taught in U.S. Pat. No. 5,062,846 to Oh et al. also include lateral bosses that are engaged by the jaws of a clip applier. A clip applier specifically designed for asymmetric plastic clips is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416 to Oh et al., also assigned to the assignee of the presently disclosed subject matter.

In addition to compatibility with sophisticated diagnostic techniques, asymmetric clips have other advantages over symmetric clips. For example, because asymmetric clips are formed from polymeric materials, the mouths of asymmetric clips can generally be opened wider than the mouths of symmetric clips. This allows a surgeon to position the clip about the desired vessel with greater accuracy. In addition, a clip of the type described in the aforementioned U.S. Pat. Nos. 4,834,096 and 5,062,846 can be repositioned before locking the clip on the vessel or before removing the clip from the vessel, in a process referred to as "approximating" the clip.

Various types of hemostatic and aneurysm asymmetric clips are used in surgery for ligating blood vessels or other tissues to stop the flow of blood. Such clips have also been used for interrupting or occluding ducts and vessels in particular surgeries such as sterilization procedures.

Applying the clip for occluding the vessel or other tissue might be the end desired result. Generally then, the clip is left in place after application to the tissue until hemostasis or occlusion occurs. At some point thereafter, the clip can be removed by using a separate instrument dedicated for that purpose, i.e., a clip removal instrument.

However, in many procedures, a vessel is occluded so that it can be safely cut. In this type of procedure, generally a vessel is clamped on both sides of the desired cut site and then the vessel is severed between the two clips. The vessel can then be anastomosed at the cut ends, or to other vessels or tissue, as required by the particular procedure. After anastomosis, the clips can be removed to restore circulation through the tissue.

Whether the clip is metallic or polymeric, it is important to leave a small cuff of tissue, typically about 1.0-3.0 mm, between the cutting face of the clip and the cut site. Without a cuff, the clip might not properly stay attached or secured in place on the vessel. For instance, the tissue could retract after cutting and pull out of the clip. Also, if the clip is applied askew, an end could pull out, resulting in leakage from the cut vessel. Further, cutting too close to the clip risks the clip being accidentally nicked, which could result in failure of the clip.

Although physicians generally desire to leave tissue cuffs on the cutting face of clips, certain situations can make this difficult. For example, in surgical sites with limited space, such as in endoscopy, the cutting zone can be very narrow, thus resulting in the placement of the clips too close to one side or the other of the cut site. Also, instances where the physician desires to preserve as much vessel as possible on the uncut face of the clip, can result in placement of the clip too close to the cut site. Finally, in close or obstructed-view surgical sites, judging the proper distance to cut from the clip can be extremely difficult.

Although polymeric ligating clips are well known in the surgical area and improvements have been made to the ligating clips, none have heretofore been designed with a mechanism to aid the physician in cutting ligated tissue properly, so that a safe length of tissue cuff remains on the cutting face of the clip. Therefore, there is believed to be a long-felt need for an improved polymeric surgical ligating clip with such a mechanism, which is particularly well suited for use in guiding a physician when cutting ligated tissue. The present disclosure is believed to provide such an improved surgical clip.

SUMMARY

In accordance with the present disclosure, a polymeric surgical clip is provided of the type comprising first and second legs joined at their proximal ends by a flexible hinge section. Each leg has a vessel clamping inner surface, an opposite outer surface, and a pair of opposing side surfaces. The vessel clamping inner surface is in opposition to the vessel clamping inner surface of the other leg. At least one cutting guide is provided on one or more of the side surfaces for aiding the physician in properly cutting the ligated tissue. Further, a female locking member is positioned on the distal end of the first leg and a male locking member is positioned on the distal end of the second leg. The female and male locking members are formed such that when the first and second leg members are moved from an open position to a closed position about the hinge section, the male locking member is lockingly engaged in the female locking member so as to removably lock the clip in the closed position.

In the preferred embodiment, the clip has a plurality of cutting guides. Preferably, the first and second legs each have at least one cutting guide disposed thereon. More preferably, at least one cutting guide is disposed on each side surface of the first and second legs. The cutting guide extends outward from the side surface to a height of at least about 3.0 mm, but can also be shorter or longer as needed. The cutting guide can have an elongated shape, whereby the length of the cutting guide is greater than its width.

The surgical clip further comprises a pair of bosses joined to opposite sides of the first leg, between the hinge section and the distal end of the first leg. The preferred embodiment also comprises a second pair of bosses joined to opposite sides of the second leg at the distal end of the second leg. A sharp tissue-penetrating tooth extends from each of the second pair of bosses outwardly towards the distal end of the first leg.

Further in the preferred embodiment, the inner vessel-clamping surface of the first leg has a concave radius of curvature and the outer surface has a convex radius of curvature between the hinge section and the distal end. In the same embodiment, the inner vessel-clamping surface of the second leg has a convex radius of curvature and the outer surface has a concave radius of curvature between the hinge section and the distal end. At least one of the inner surfaces of the clip comprises a plurality of protrusions extending from the inner surface, for providing improved vessel retention during and following closure of the clip. Preferably, both of the inner surfaces comprise the plurality of protrusions.

The surgical clip disclosed herein is most suitably made of polymeric material and accordingly minimizes interference with high technology diagnostic modalities such as CAT SCAN, MRI and MRS. At the same time, the clip is nearly as small as comparable metal clips while maintaining sufficient strength and possessing a high degree of security in the clip's latching mechanism. The surgical clip is further configured to provide a mechanism for guiding a physician through cutting of the clamped vessel so that a tissue cuff is created.

It is therefore an object of the presently disclosed surgical clip to provide a polymeric surgical clip capable of occluding a vessel and guiding a physician when cutting the vessel so that a tissue cuff of proper length is created.

It is a further object to provide a polymeric surgical clip for guiding a physician in cutting a vessel to produce a tissue cuff of proper length, wherein the clip comprises a cutting guide extending outward from and disposed along at least a portion of the length of one or both side surfaces of one or both of the first and second legs thereof.

Some of the objects of the subject matter disclosed herein having been stated hereinabove, other objects will become evident as the description proceeds when taken in connection with the accompanying drawings as best described hereinbelow.

DETAILED DESCRIPTION

Referring first to FIGS. 1-5 of the drawings, one example is illustrated of an asymmetric surgical clip with a cutting guide, generally designated 12, that is suitable for use in conjunction with the presently disclosed subject matter. Clip 12 and others of similar design are particularly useful as hemostatic clips that can be latched around a vessel or other type of tissue to ligate the vessel and thereby stop or reduce the flow of fluid through the vessel. Clip 12 can be constructed from any suitable biocompatible material, such as certain metals and polymers. However, the presently disclosed subject matter is particularly suitable for practice with polymeric clips. Thus, clip 12 preferably comprises a one-piece integral polymeric body formed from a suitable strong biocompatible engineering plastic such as the type commonly used for surgical implants. Examples include, but are not limited to, acetal polyoxymethylene (POM), polyethylene terephthalate (PET), polybutylene terephthalate (PBT), polyoxymethylene, or other thermoplastic materials having similar properties that can be injection-molded, extruded or otherwise processed into like articles.

Figure 1:
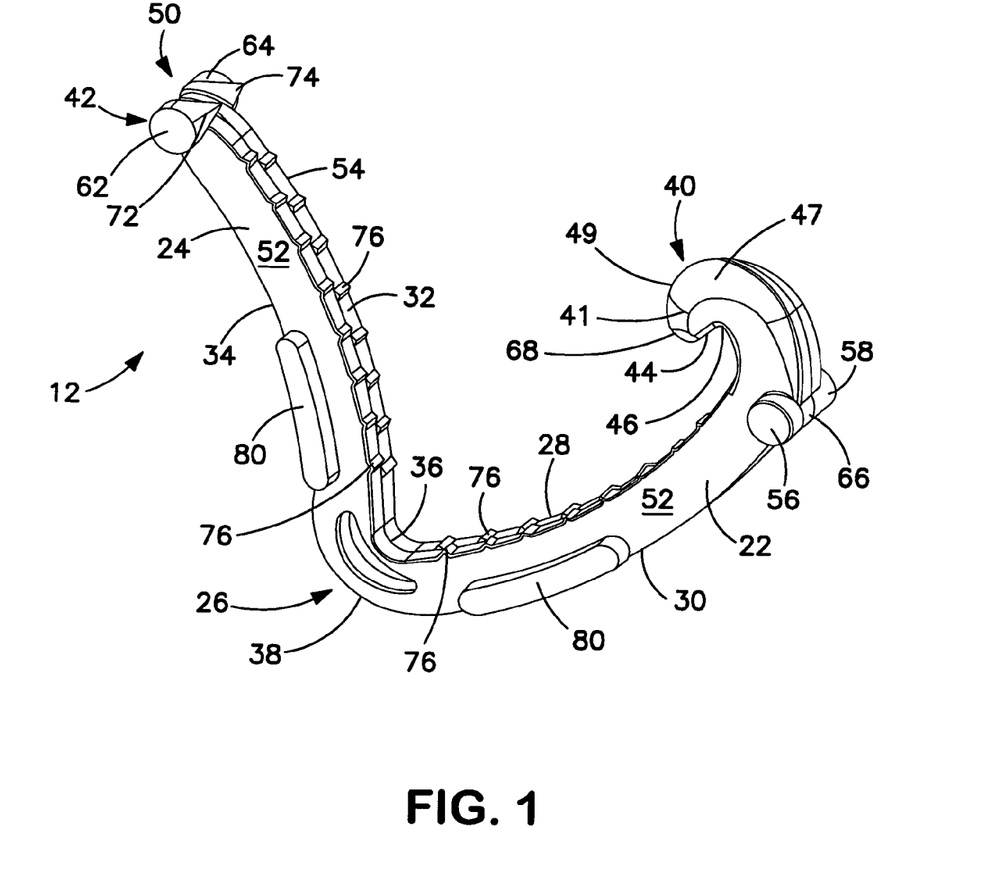
FIG. 1 is a perspective view of the improved surgical ligating clip of the present invention with a surgical cutting guide.

Now turning to FIG. 1, the body of clip 12 comprises a first or outer leg, generally designated 22, and a second or inner leg, generally designated 24. First and second legs 22 and 24 are joined at their proximal ends by an integral hinge section, generally designated 26. First and second legs 22 and 24 each have a pair of opposing side surfaces 52 and 54. First and second legs 22 and 24 also have complementary arcuate profiles. Thus, first leg 22 has a concave inner surface 28 and a convex outer surface 30, and second leg 24 has a convex inner surface 32 and a concave outer surface 34. Convex inner surface 32 of second leg 24 and concave inner surface 28 of first leg 22 have substantially matching radii of curvature.

Hinge section 26 has a continuous concave inner surface 36 and a continuous convex outer surface 38. Concave inner surface 36 of hinge section 26 joins concave inner surface 28 of first leg 22 and convex inner surface 32 of second leg 24. Convex outer surface 38 of hinge section 26 joins convex outer surface 30 of first leg 22 and concave outer surface 34 of second leg 24.

First leg 22 terminates in a female locking member 40 at its distal end. Female locking member 40 comprises a resilient inwardly turned hook 41. Second leg 24 terminates in a male locking member 50. Male locking member 50 comprises a pointed tip section 42 at its distal end. Hook 41 is distally curved inwardly toward hinge section 26, and has a transverse beveled surface 44. Beveled surface 44 and concave inner surface 28 define a latching recess 46, which is adapted for conformally engaging tip section 42 of male locking member 50 in the course of compressing clip 12 into a latched or locked position around a vessel or other tissue.

Figure 2:
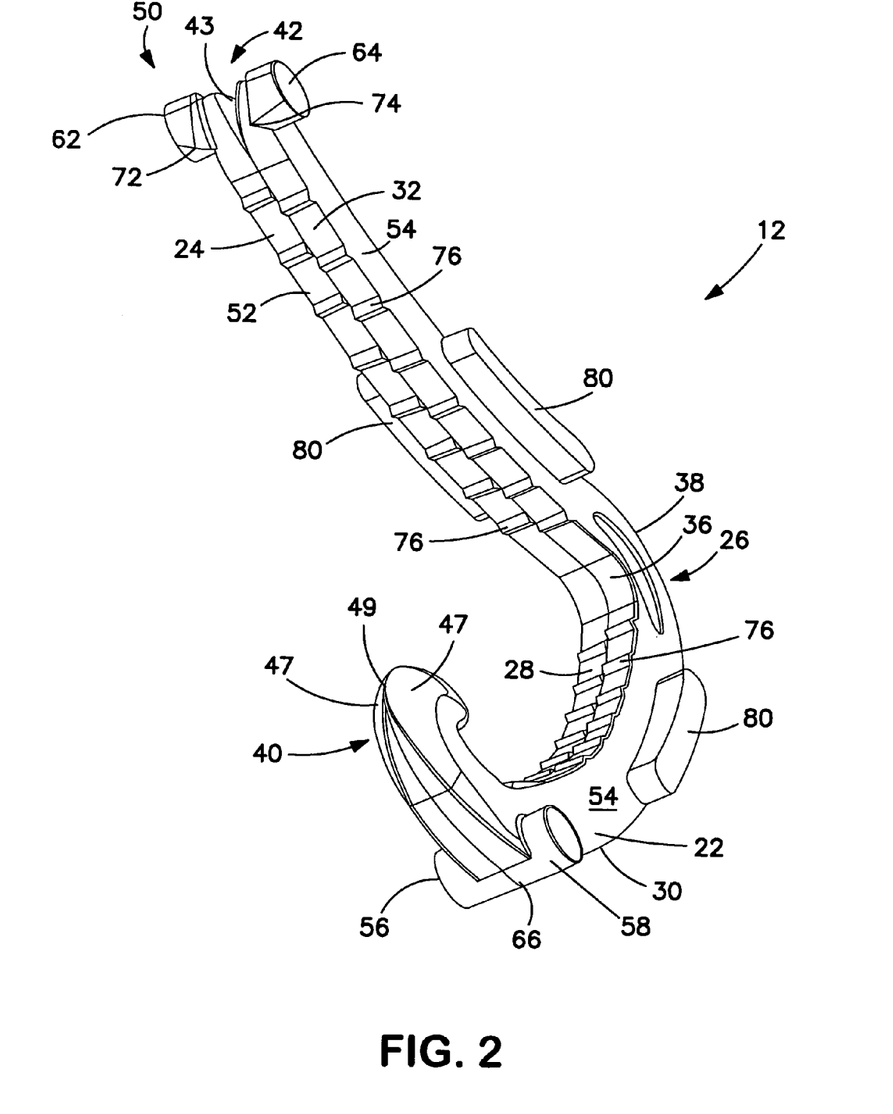
FIG. 2 is a second perspective view of the surgical ligating clip.

As best shown in FIG. 2, the top surface of hook 41 preferably comprises two convex surfaces 47 that come together to define a sharp crest-like cutting edge 49 to facilitate cutting through connective tissue adjacent a vessel or other tissue during latching of the clip therearound.

Figure 3:
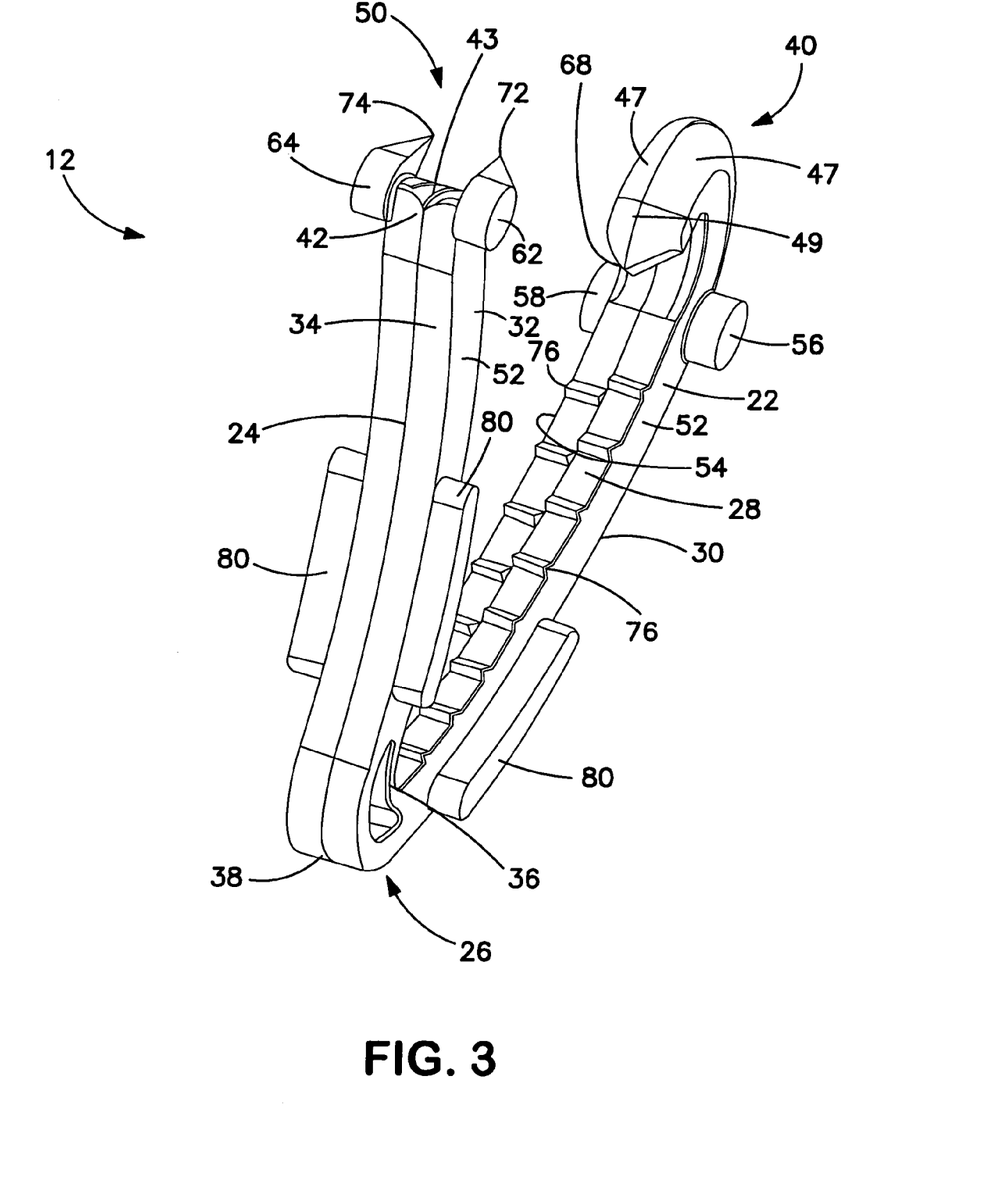
FIG. 3 is a third perspective view of the surgical ligating clip.

As best shown in FIG. 3, which is a view directed into the open concave side of clip 12, clip 12 comprises opposing side surfaces 52 and 54. Typically, the body of clip 12 has a constant thickness between side surfaces 52 and 54. Adjacent to the distal end of the first leg 22 and immediately inwardly of hook 41, a pair of cylindrical bosses 56 and 58 are formed coaxially on the opposed side surfaces 52 and 54, respectively, of first leg 22. In the illustrated example of clip 12, a bridge section 66 couples bosses 56 and 58 together. As evident in FIG. 2, bosses 56 and 58 project outwardly beyond convex outer surface 30 of first leg 22.

Referring again to FIG. 3, at the distal end of second or inner leg 24, another pair of cylindrical bosses 62 and 64 is formed coaxially on the opposed lateral surfaces of inner leg 24 at tip section 42. As evident in FIG. 3, bosses 62 and 64 of second leg 24 extend longitudinally forward beyond tip section 42.

Also, as best shown in FIG. 3, hook 41 of first leg 22 preferably terminates at a sharp tip 68 with cutting edge 49 extending at least along a portion of the length of the top surface of hook 41. Male locking member 50 of second leg 24 includes a pair of inwardly directed sharp tissue-penetrating teeth 72 and 74, to assist in gripping, stretching and piercing nearby connective tissue, in concert with cutting edge 49 and sharp tip 68 on hook 41.

Both first and second legs 22 and 24 have a plurality of protrusions or teeth 76 extending from their respective inner surfaces 28 and 32. These features are designed to engage the tissue of the vessel being clamped and assist in preventing the vessel from sliding laterally or longitudinally during or following clip closure. It will be noted, however, that other clips equally suitable for use in conjunction with the presently disclosed subject matter may not contain such features.

Figure 5:
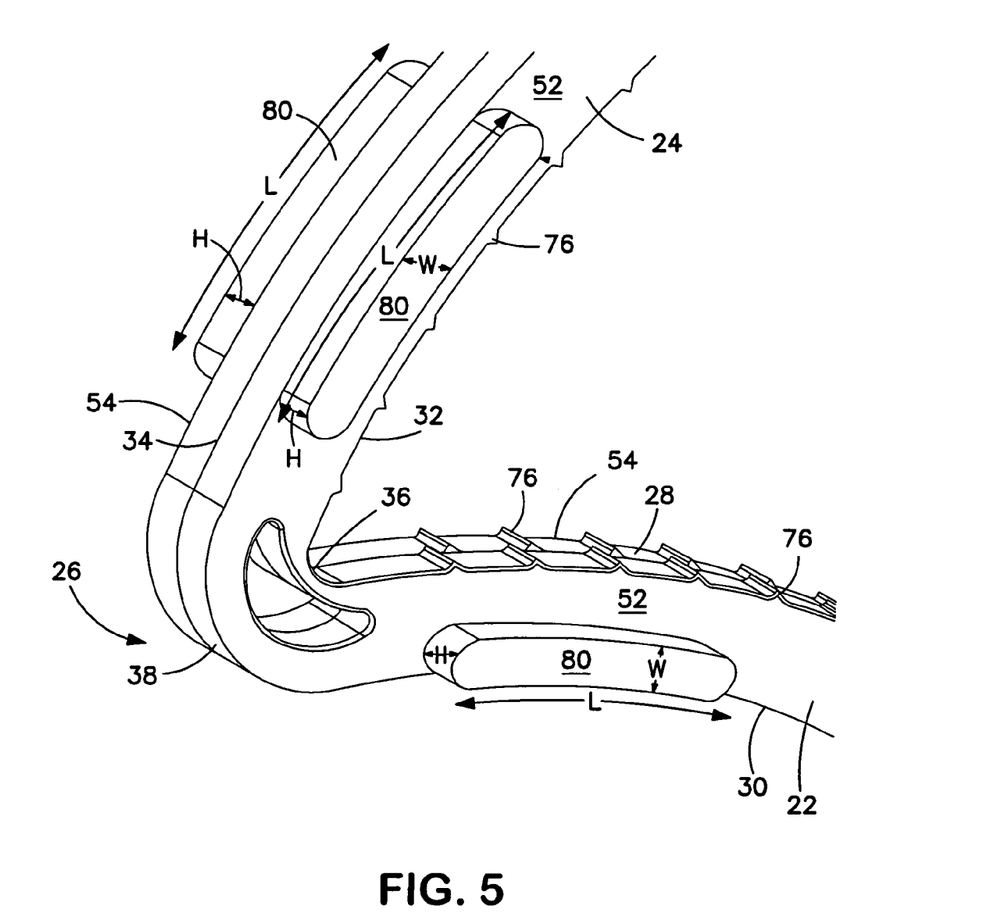
FIG. 5 is an enlarged perspective view of the surgical ligating clip showing the hinge section and proximal ends of the first and second legs in detail including three cutting guides.

As best shown in FIG. 5, clip 12 further comprises a plurality of integral cutting guides 80 extending outward from and disposed along at least a portion of both side surfaces 52 and both side surfaces 54. Cutting guides 80 are designed to aid the physician in cutting the ligated vessel or tissue properly, such that a tissue cuff of safe length (typically about 1.0-3.0 mm) is produced. Cutting guides 80 have a height H of 3.0 mm or less extending out from side surfaces 52 and 54 of clip 12. Height H varies depending on the desired size of the cuff produced after the vessel is cut. As height H increases, so does the length of the tissue cuff, and vice versa with decreasing height H. Cutting guides 80 have a length L in the lengthwise direction of first and second legs 22 and 24 that varies according to need. One of skill in the art will appreciate different benefits to different lengths L, and the presently disclosed subject matter is intended to be inclusive of these variations based on design choice.

In a preferred embodiment, length L is sufficient to provide a stable guide against which the cutting implement can rest during the cut. It is envisioned that length L can be as great as the length of opposing side surface 52 or 54, but no longer since otherwise it would interfere with the proper functioning of female and male locking members 40 and 50 and/or hinge section 26 (or even bosses 56, 58, 62 and 64, if present). However, this is rarely desirable since it could decrease the flexibility of first and second legs 22 and 24, which is necessary for optimal functioning of clip 12. In the preferred embodiment shown in FIGS. 1-5, length L is half or less the length of lateral sides 52 and 54.

In an alternative embodiment, length L can be much less than what is required for guiding the cutting implement if more than one cutting guide 80 is present in a spaced-apart relationship along the same lateral side 52 or 54. In this embodiment, spaced apart cutting guides 80 work together as one cutting guide 80 to guide the cutting implement. This arrangement requires less material, thereby having less impact on the overall flexibility of clip 12. It is envisioned that in an alternative embodiment, bosses 56, 58, 62 and 64 can have the same height as cutting guide 80, and thereby also function in concert with cutting guide 80 as additional spaced-apart cutting guides 80. However, it is noted that bosses 56, 58, 62 and 64 cannot alone function as cutting guides 80, since they do not have a length great enough to provide a stable platform for guiding the cutting implement. Further, they cannot be lengthened enough to function as guides by themselves, since then they would not be able to function as bosses for a clip applying instrument 120, as described in detail below and shown in FIGS. 6A-6C. Therefore, only in an embodiment where bosses 56, 58, 60 or 62 have a height identical to height H of cutting guides 80 and are in a spaced-apart relationship on the same opposing sides 52 and 54 with cutting guides 80 can bosses 56, 58, 60 or 62 act in concert with cutting guides 80 as additional spaced-apart cutting guides 80.

Cutting guides 80 have a width W that can be as great as the width of side surfaces 52 and 54. A width W greater than the width of side surfaces 52 and 54 could interfere with clamping the vessel, and therefore is not desirable. In a preferred embodiment, width W is only as great as is needed to properly function as a guide to the cutting implement, e.g. such that cutting guides 80 will not collapse under the pressure of the cutting implement resting against it. A minimal width W is desirable so that the flexibility of first and second legs 22 and 24 is minimally impacted. In the illustrated preferred embodiment, width W is approximately half the width of side surfaces 52 and 54.

Figure 4:
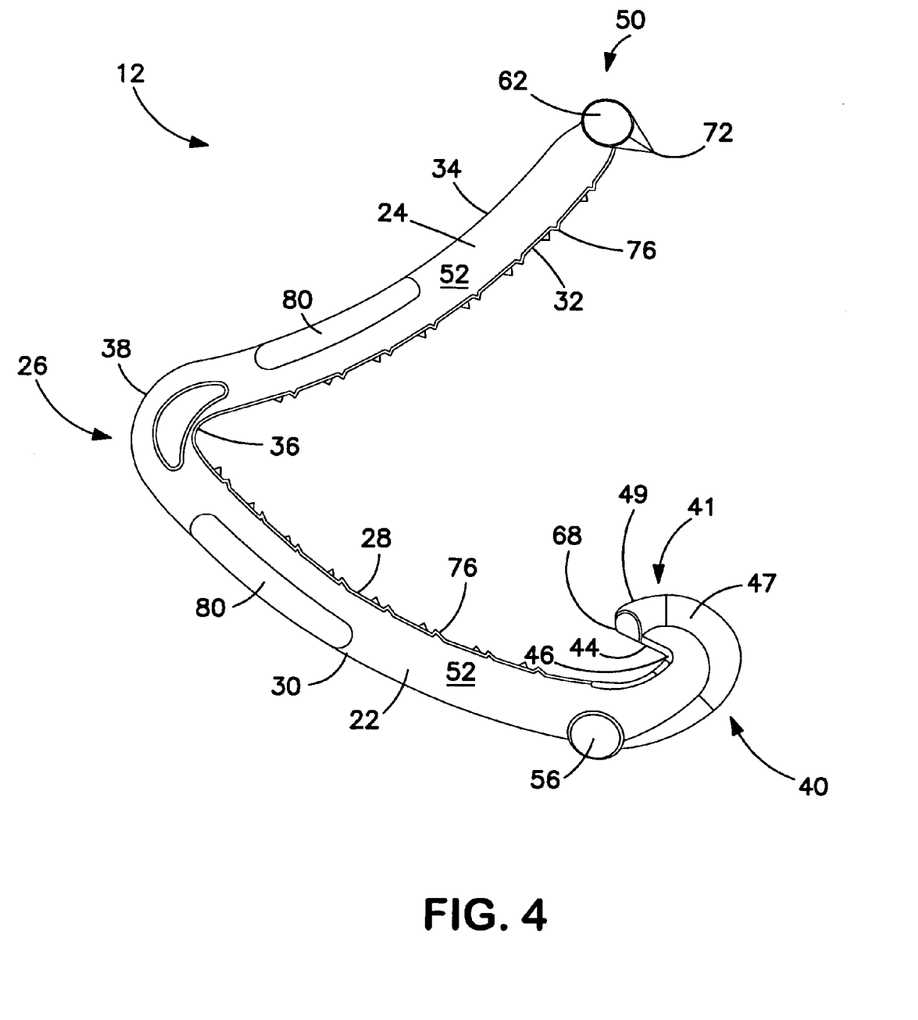
FIG. 4 is a side elevation view of the surgical ligating clip showing the positioning of two cutting guides.

Cutting guides 80 can be positioned anywhere along the length of side surfaces 52 and 54. In the preferred embodiment, as best shown in FIG. 4, cutting guides 80 are positioned adjacent, but not encroaching onto, hinge section 26. This position is especially preferable if boss 56, 58, 62 or 64 can double as a 'surrogate' spaced-apart cutting guide 80, as described above. Alternatively, one or more additional cutting guides 80 in spaced-apart arrangement can be positioned along the surface of the same side surfaces 52 and 54.

The preferred embodiment of clip 12 has a cutting guide 80 on each of the four side surfaces 52 and 54. In an alternative embodiment, Clip 12 can have only one (or more) cutting guide(s) 80 on just one side surface 52 or 54 of only one or both of legs 22 or 24, if desirable, for a particular application. For example, a specialty clip 12 can be designed for a particular application where specific placement of clip 12 is imperative. In such a scenario, it could be preferable to have cutting guide 80 placed at a particular site, e.g. on only one side surface 52 or 54 of one or both first and second legs 22 and 24, as a marker for the physician to properly position clip 12, or as a reminder of where to cut after positioning. Alternatively, it may be desirable for clip 12 to have one or more cutting guides 80 on each side surface 52 and 54 (as exemplified in FIGS. 1-5) so that the physician need not pay particular attention to the positioning of clip 12 or on which side of clip 12 the cut is made. Both embodiments and combinations thereof are envisioned by the present invention.

Clip Closure

In the practice of ligating and cutting a vessel or other tissue, as understood by persons skilled in the art, clip 12 is designed to be compressed into a latched or locked closed position around the vessel through the use of an appropriate clip applicator instrument, such as the type described in the aforementioned U.S. Pat. No. 5,100,416. The clip applicator instrument engages bosses 56, 58, 62 and 64 of clip 12 and pivots bosses 56, 58, 62 and 64 inwardly about hinge section 26. This causes first and second legs 22 and 24 to close around the vessel, with convex inner surface 32 of second leg 24 and complementary concave inner surface 28 of first leg 22 contacting the outer wall of the vessel.

However, before any contact is made between first and second legs 22 and 24, sharp tissue penetrating teeth 72 and 74 on bosses 62 and 64 of second leg 24 start to indent and penetrate any connective tissue surrounding the vessel therebetween and pull the tissue down. Simultaneously, sharp tip 68 and hook 41 on first leg 22, while sliding between teeth 72 and 74, also begin to penetrate the tissue and force the tissue up. Sharp tip 68 and cutting edge 49 on hook 41 enter a groove 43 of pointed tip section 42 on second leg 24, thereby beginning puncturing and cutting of the connective tissue.

As cutting edge 49 and sharp tip 68 of hook 41 continue to move through groove 43 between teeth 72 and 74, shear forces contribute to further puncturing and cutting of the connective tissue surrounding the vessel. If all the tissue is still not cut between the distal portion of second leg 24 and hook 41, it will stretch and become thinner until it is easily punctured by sharp tip 68 and cut by cutting edge 49 of hook 41 as it passes through groove 43 of second leg 24. Once the connective tissue is cut, female and male locking members 40 and 50 are able to lockingly engage without interference.

Tip section 42 of second leg 24 then begins to contact female locking member 40 at hook 41. Further pivotal movement by the applicator instrument longitudinally elongates first leg 22 and deflects hook 41, allowing tip section 42 of male locking member 50 to align with latching recess 46. Upon release of the applicator instrument, tip section 42 snaps into and is conformably seated in latching recess 46, at which point clip 12 is in its latched and closed position. In the latched condition, tip section 42 is engaged between concave inner surface 28 and beveled surface 44, thereby securely clamping a designated vessel or other tissue between concave inner surface 28 and convex inner surface 32.

After clip 12 is secured in its closed position and the vessel is ligated, most likely with two clips 12 on either side of the cutting site, the physician can safely cut the vessel. With prior art clips, as discussed hereinabove, the cutting step is potentially dangerous, as cutting too close to the clip can result in an unsafely short tissue cuff, no tissue cuff, or even nicking and damaging clip 12. The presently disclosed clip 12 eliminates these dangers through incorporation of one or more cutting guides 80 on one or more side surfaces 52 and 54 of one or both legs 22 and 24, as discussed herein above. In use, the physician simply abuts the cutting implement against the outer surface of cutting guides 80 and proceeds to sever the vessel with the braced cutting implement. The cutting implement is automatically aligned an optimal distance away from clip 12 so that a tissue cuff of proper size is produced.

Prior art clips similar to clip 12 are described in detail in the commonly assigned U.S. Pat. No. 4,834,096 to Oh et al. and 5,062,846 to Oh et al., the disclosures of which are incorporated herein in their entireties. In addition, a particularly suitable clip is the HEM-O-LOK® clip commercially available from the assignee of the presently disclosed subject matter. These clips are currently available in sizes designated "M", "ML", "L" and "XL". The clip cartridge described hereinbelow can be adapted to accommodate any sizes of HEM-O-LOK® clips commercially available.

Figure 6A:
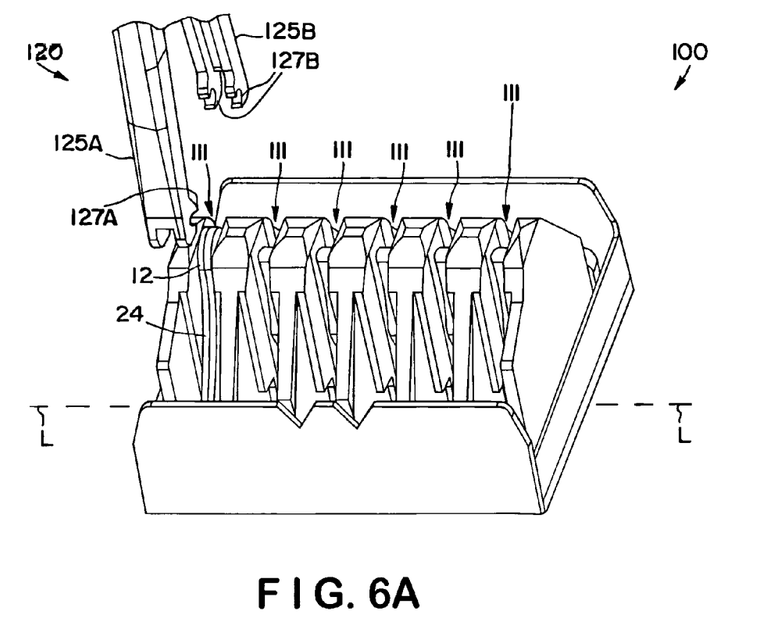
FIG. 6A is a perspective view of a clip applier being inserted into a compartment of a clip cartridge to engage a surgical ligating clip provided in accordance with the present invention.
Figure 6B:
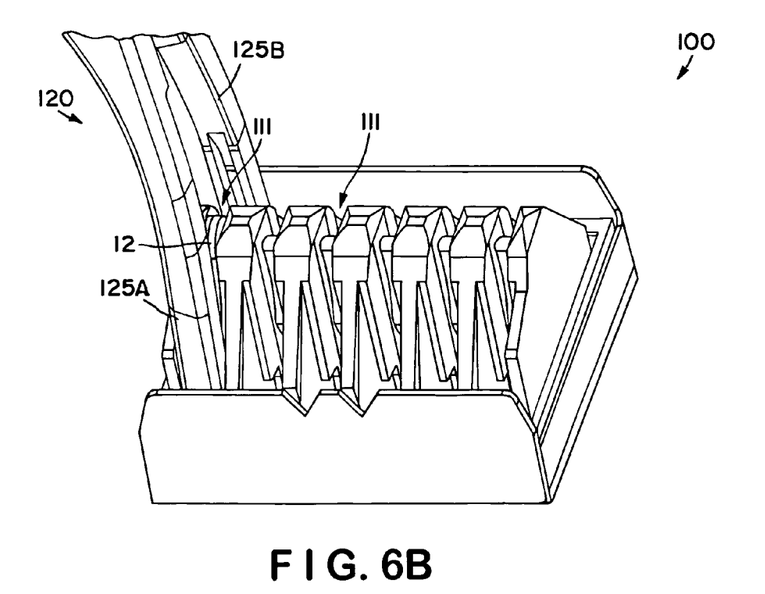
FIG. 6B is another perspective view showing the clip applier engaging the surgical ligating clip loaded in one of the compartments of the clip cartridge as shown in FIG. 6A.
Figure 6C:
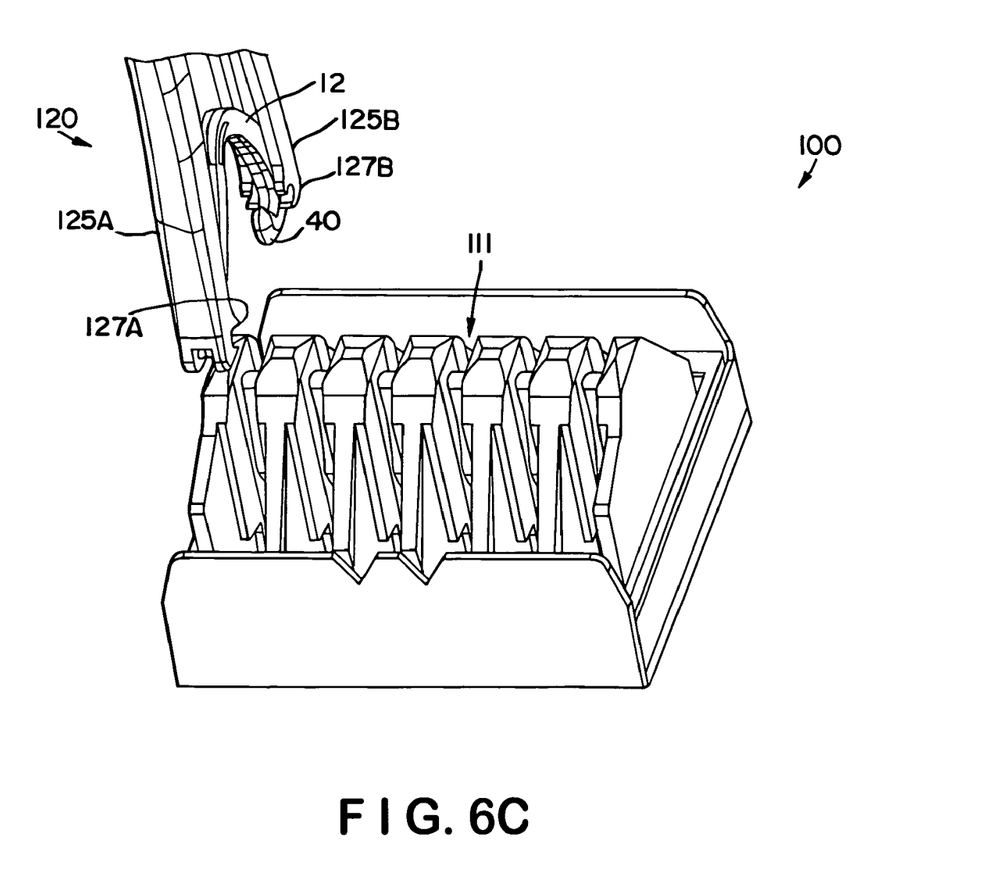
FIG. 6C is another perspective view showing the clip applier extracting the surgical ligating clip from the compartment of the clip cartridge shown in FIG. 6A.

Referring now to FIGS. 6A-6C, a preferred embodiment of a clip cartridge, generally designated 100, is shown for use with clip 12. Clip cartridge 100 preferably is constructed from a single-molded plastic body from which several features are formed. In particular, clip cartridge 100 comprises a plurality of clip retaining chambers or compartments 111 spaced along a longitudinal axis A of clip cartridge 100. Each clip compartment 111 is substantially identical and adapted for storing one clip 12, which preferably has an asymmetric design with cutting guides 80, 81, 82 and 83 as described above and illustrated in FIGS. 1-5. FIG. 6A illustrates one clip 12 in a stored condition in one of clip compartments 111. It will be understood, however, that preferred embodiments of clip cartridge 100 include several clip compartments 111 for storing several clips 12. For instance, clip cartridge 100 is adapted for storing six clips 12, although other embodiments can be provided that store more or less clips 12. If desired, an adhesive backing (not shown) can be provided on the underside of clip cartridge 100 to facilitate securing clip cartridge 100 to a tray or other supporting component during use.

FIGS. 6A-6C also illustrate the distal end of a representative clip applying instrument for clip 12, generally designated 120, comprising opposing pivotable jaws 125A and 125B. Jaws 125A and 125B have respective jaw recesses 127A and 127B adapted to engage and retain bosses 56, 58, 62 and 64 of clip 12 (see FIGS. 1-5). According to a method provided herein, FIG. 6A illustrates clip applying instrument 120 in a position over clip 12 prior to inserting clip applying instrument 120 into a selected clip compartment 111. FIG. 6B illustrates clip applying instrument 120 being inserted into selected clip compartment 111 to load clip 12 into locking engagement with clip applying instrument 120 (with bosses 56, 58, 62 and 64 retained in jaw recesses 127A and 127B). FIG. 6C illustrates the subsequent step of extracting clip 12 from clip cartridge 100 by removing clip applying instrument 120 with clip 12 loaded therein.

It will be understood that various details of the presently disclosed subject matter can be changed without departing from the scope of the disclosure. Furthermore, the foregoing description is for the purpose of illustration only, and not for the purpose of limitation—the invention being defined by the claims.

What is claimed is:

1. A surgical clip with an integral cutting guide, comprising:
   (a) a first leg and a second leg, each of said legs having an inner vessel-clamping surface, an outer surface and a pair of opposing side surfaces flanking said inner and outer surfaces, said inner surfaces being positioned in opposition to each other;
   (b) a flexible hinge section integrally disposed between and joining the proximal ends of said first and second legs;
   (c) at least one cutting guide extending outward from and disposed along at least a portion of the length of at least one of said opposing side surfaces on at least one of said first and second legs, the at least one cutting guide being a raised flat platform having an angular cross-sectional profile in a plane extending through both opposing side surfaces and substantially parallel to said inner vessel-clamping surface; and
   (d) a female locking member positioned on the distal end of said first leg and a male locking member positioned on the distal end of said second leg, said female and male locking members being formed whereby when said first and second leg members are moved from an open position to a closed position about said hinge section, said male locking member is lockingly engaged in said female locking member so as to removably lock said first and second leg members of said surgical clip in said closed position, wherein the at least one cutting guide includes a substantially flat exterior edge to provide a stable platform for guiding a cutting implement.

2. The surgical clip of claim 1, wherein said at least one cutting guide comprises a plurality of cutting guides, wherein said first and second legs each have at least one of said plurality of cutting guides disposed thereon.

3. The surgical clip of claim 2, wherein at least one of said cutting guides is disposed on each of said opposing side surfaces.

4. The surgical clip of claim 1, wherein said at least one cutting guide extends outward from said side surface to a height of about 3.0 mm or less.

5. The surgical clip of claim 1, wherein said at least one cutting guide has an elongated shape, whereby the length of said cutting guide is greater than the width of said cutting guide.

6. The surgical clip of claim 1, further comprising a pair of bosses joined to opposite sides of said first leg between said hinge section and the distal end of said first leg, and a pair of bosses joined to opposite sides of said second leg at the distal end of said second leg.

7. The surgical clip of claim 6, wherein said at least one cutting guide is disposed along at least a portion of the length of at least one of said opposing side surfaces between said hinge section and said bosses.

8. The surgical clip of claim 7, wherein said at least one cutting guide is disposed adjacent said hinge section along at least a portion of the length of at least one of said opposing side surfaces.

9. The surgical clip of 6, wherein a portion of said pair of bosses joined to said first leg extend beyond said outer surface of said first leg to form a bridge section.

10. The surgical clip of claim 6, wherein said pair of bosses on said second leg each have a sharp tissue-penetrating tooth extending outwardly therefrom toward said first leg.

11. The surgical clip of claim 1, wherein said inner surface of said first leg has a concave radius of curvature between said hinge section and its distal end, said outer surface of said first leg has a convex radius of curvature between said hinge section and its distal end, said inner surface of said second leg has a convex radius of curvature between said hinge section and its distal end, and said outer surface of said second leg has a concave radius of curvature between said hinge section and its distal end.

12. The surgical clip of claim 1, wherein at least one of said inner surfaces of said clip comprises a plurality of protrusions extending from said inner surface for providing improved vessel retention during and following closure of said clip.

13. The surgical clip of claim 12, wherein both of said inner surfaces of said clip comprise said plurality of protrusions.

14. The surgical clip of claim 1, wherein said hinge section has a continuous concave inner surface and a continuous convex outer surface.

15. The surgical clip of claim 1, wherein said female locking member comprises a resilient inwardly turned hook curved toward said second leg member.

16. The surgical clip of claim 15, wherein said male locking member is complementary to said hook of said female locking member whereby when said first and second leg members are moved from an open position to a closed position about said hinge section, said resilient hook of said female locking member contacts said male locking member and is urged open to receive said male locking member so as to removably lock said first and second leg members of said surgical clip in said closed position.

17. A surgical clip with an integral cutting guide, comprising:

(a) a first leg and a second leg, each of said legs having an inner vessel-clamping surface, an outer surface and a pair of opposing side surfaces flanking said inner and outer surfaces, said inner surfaces being positioned in opposition to each other;

(b) a flexible hinge section integrally disposed between and joining the proximal ends of said first and second legs;

(c) a plurality of cutting guides, each extending outward from and disposed along at least a portion of the length of each of said opposing side surfaces of each of said first and second legs, wherein each cutting guide includes a substantially flat exterior edge to provide a stable platform for guiding a cutting implement, each of the plurality of cutting guides being a raised flat platform having an angular cross-sectional profile in a plane extending through both opposing side surfaces and substantially parallel to said inner vessel-clamping surface; and (d) a female locking member positioned on the distal end of said first leg and a male locking member positioned on the distal end of said second leg, said female and male locking members being formed whereby when said first and second leg members are moved from an open position to a closed position about said hinge section, said male locking member is lockingly engaged in said female locking member so as to removably lock said first and second leg members of said surgical clip in said closed position.

18. The surgical clip of claim 17, wherein each of said cutting guides extends outward from said side surface to a height of about 3.0 mm or less.

19. The surgical clip of claim 17, wherein each of said cutting guides has an elongated shape, whereby the length of said cutting guide is greater than the width of said cutting guide.

20. The surgical clip of claim 17, further comprising a pair of bosses joined to opposite sides of said first leg between said hinge section and the distal end of said first leg, and a pair of bosses joined to opposite sides of said second leg at the distal end of said second leg.

21. The surgical clip of claim 20, wherein each of said cutting guides is disposed along at least a portion of the length of a corresponding one of said opposing side surfaces between said hinge section and said bosses.

22. The surgical clip of claim 21, wherein each of said cutting guides is disposed adjacent said hinge section along at least a portion of the length of a corresponding one of said opposing side surfaces.

23. The surgical clip of 20, wherein a portion of said pair of bosses joined to said first leg extend beyond said outer surface of said first leg to form a bridge section.

24. The surgical clip of claim 20, wherein said pair of bosses on said second leg each have a sharp tissue-penetrating tooth extending outwardly therefrom toward said first leg.

25. The surgical clip of claim 17, wherein said inner surface of said first leg has a concave radius of curvature between said hinge section and its distal end, said outer surface of said first leg has a convex radius of curvature between said hinge section and its distal end, said inner surface of said second leg has a convex radius of curvature between said hinge section and its distal end, and said outer surface of said second leg has a concave radius of curvature between said hinge section and its distal end.

26. The surgical clip of claim 17, wherein at least one of said inner surfaces of said clip comprises a plurality of protrusions extending from said inner surface for providing improved vessel retention during and following closure of said clip.

27. The surgical clip of claim 26, wherein both of said inner surfaces of said clip comprise said plurality of protrusions.

28. The surgical clip of claim 17, wherein said hinge section has a continuous concave inner surface and a continuous convex outer surface.

29. The surgical clip of claim 17, wherein said female locking member comprises a resilient inwardly turned hook curved toward said second leg member.

30. The surgical clip of claim 29, wherein said male locking member is complementary to said hook of said female locking member whereby when said first and second leg members are moved from an open position to a closed position about said hinge section, said resilient hook of said female locking member contacts said male locking member and is urged open to receive said male locking member so as to removably lock said first and second leg members of said surgical clip in said closed position.

* * * * *